United States Patent
Akbarali et al.

(10) Patent No.: US 6,653,494 B2
(45) Date of Patent: Nov. 25, 2003

(54) PROCESSES FOR PRODUCING TRIARYL PHOSPHITE

(75) Inventors: Padiyath Mohammed Akbarali, New Mangalore (IN); Kuniyil Kulangara Vijay Raj, New Mangalore (IN); Karabasana T. Gouda, New Mangalore (IN); Ramachandran Radhakrishnan, Bangalore (IN)

(73) Assignee: Strides Inc., Somerset, NJ (US)

( * ) Notice: Subject to any disclaimer, the term of this patent is extended or adjusted under 35 U.S.C. 154(b) by 0 days.

(21) Appl. No.: 10/210,922

(22) Filed: Aug. 2, 2002

(65) Prior Publication Data

US 2003/0100787 A1 May 29, 2003

(30) Foreign Application Priority Data

Nov. 26, 2001 (IN) .................... 1128/MUM/2001

(51) Int. Cl.$^7$ .................................................. C07F 9/02
(52) U.S. Cl. ........................................................ 558/96
(58) Field of Search ............................................ 558/96

(56) References Cited

U.S. PATENT DOCUMENTS

| | | | |
|---|---|---|---|
| 3,533,989 A | 10/1970 | Wescott, Jr. | |
| 3,644,536 A | 2/1972 | Bafford | |
| 4,312,818 A | 1/1982 | Maul et al. | |
| 4,321,218 A | 3/1982 | Rasberger et al. | |
| 4,360,617 A | 11/1982 | Müller et al. | |
| 4,440,696 A | 4/1984 | Maul et al. | |

FOREIGN PATENT DOCUMENTS

| | | | |
|---|---|---|---|
| DE | 2046200 | | 3/1971 |
| DE | 2940620 | | 4/1981 |
| DE | 2940620 A1 | * | 4/1981 |
| DE | 2702661 | | 8/1987 |
| EP | 0455092 | | 11/1991 |

OTHER PUBLICATIONS

Mayer et al., 1981, "Triaryl phosphites", CAS:1981:442644.*

* cited by examiner

Primary Examiner—Joseph K. McKane
Assistant Examiner—Rei Tsang Shiao
(74) Attorney, Agent, or Firm—Volpe and Koenig, P.C.

(57) ABSTRACT

A one pot process for the preparation of sterically hindered triaryl phosphite is provided. It is suitable for large scale commercial production with an advantage of having carried out the reaction at 0–5° C. in a shortest time of 1 hr using pyridine as Lewis base to remove HCl formed in the reaction; thus avoiding the usage of scrubber. The triaryl phosphite is of the formula $P(OR)_3$ and is produced by reacting a di alkyl—substituted phenol of formula ROH with phosphorus trihalide in a presence of a Lewis base, wherein R represents an aryl compound of a formula $C_6H_3RaRb$, wherein Ra is tertiary alkyl, Rb is lower alkyl or tertiary alkyl. The process preferably comprises of mixing a stoichiometric amount of 2,4-dialkyl phenol with phosphorous trihalide in methylene chloride with different stoichiometric amounts of pyridine such as the molar equivalent, 10 mol %, 20 mol % and 50 mol % more than the amount of 2,4 dialkyl phenol. The reaction is preferably carried out at 0–5° C. and takes only 1 hr for the completion, followed by a precipitation out of isopropanol.

28 Claims, No Drawings

PROCESSES FOR PRODUCING TRIARYL PHOSPHITE

FIELD OF THE INVENTION

This invention relates to processes for producing triaryl phosphite. More particularly, this invention relates to processes for producing large quantities of hindered triaryl phosphite.

BACKGROUND OF THE INVENTION

The commercial use of triaryl phosphites in relation to latex is well known in the art. Triaryl phosphites containing alkyl-substituted phenyl rings are found to be effective synthetic latex stabilizers and are preferred over simpler aryl phosphites for several various reasons. One such reason is that it is non-discoloring. Yet another reason is that it imparts fewer odors to the finished polymer. Further, it is also more resistant to hydrolysis, which makes its addition possible to the latter as aqueous emulsions.

These important commercial uses of the triaryl phosphites have given rise to the development of research in this area intended to produce the same at cost efficient manners.

The preparation of ortho tertiary alkyl aryl phosphites is more difficult than the preparation of phosphites containing less hindered substituents. In fact it has been proved that it impossible to obtain acceptable yields of good quality hindered aryl phosphites in the absence of heterocyclic catalysts.

The following diagram illustrates the preparation of tris dietary alkyl aryl phosphite of general formula $P(OR)_3$ by reacting a di alkyl substituted phenol of formula ROH where R represents $C_6H_3R_aR_b$.

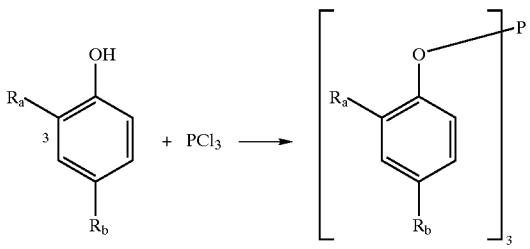

$R_a$ is tertiary alkyl, $R_b$ is lower alkyl or tertiary alkyl.

Various processes for the preparation of triaryl phosphite have been disclosed in prior patent disclosures. The U.S. Pat. No. 3,533,989 to Wescott Jr. discloses a process for the preparation of triaryl phosphite. According to this patent, certain basic materials such as triethylamine have been used in stoichiometric quantities as a hydrogen chloride scavenger so as to give yields as high as 80% of the theory of the desired product. It is not desirable to use a stoichiometric quantity of triethylamine in the preparation of the cited phosphite compound.

U.S. Pat. No. 4,312,818 to Maul et al. describes a process for producing triaryl phosphite from phosphorous trihalides and alkyl substituted phenol in the ring of formula ROH of where $R=C_6H_3R_aR_b$ ($R_a$ is tertiary alkyl, $R_b$ is lower alkyl or tertiary alkyl) with the use of specific phosphorous-, nitrogen and/or sulfur containing compounds as catalysts has been disclosed.

U.S. Pat. No. 4,440,696 to Maul et al. describes another process for producing triaryl phosphite. According to this process, the catalyst is selected from the group consisting of an amide of a carboxylic acid.

The use of alkylated triaryl phosphites as stabilizers against thermo-oxidative and light-induced degradation of organic material has been disclosed in U.S. Pat. No. 4,321,218 to Rasberger et al.

U.S. Pat. No. 4,360,617 to Muller et al. describes the use of triaryl phosphite in combination with phenolic antioxidants for stabilizing organic polymers. The corresponding German Patent No. 2,702661 also discloses stabilizer systems of triaryl phosphite and phenols.

European Patent Application EP0455092 to Gregory et al. describes suspensions of polymer additives in functional fluids and thermoplastic resin compositions containing the same.

A process for the preparation of tris (2,4-ditertiary butyl phenyl) phosphite involving the heating of 0.8 mole of required phenol with 0.2 mole of $PCl_3$ for 1 hour at 80° C. and for 8 hour at 200° C. has been disclosed in German Patent No. 2,046,200.

German Patent No. 2,940,620 to Mayer et al. describes the preparation of tris (2,4-ditertiary butyl phenyl) phosphite by treating corresponding phenol with $PCl_3$ at 50° C. and then at 130° C. The process disclosed in this case requires a temperature level of 130° C. for a continuous period. Also the process requires evolution of hydrogen chloride gas which requires scrubbing.

SUMMARY OF THE PRESENT INVENTION

An improved one pot process for the preparation of sterically hindered triaryl phosphites is provided, which produce high yields and quality products, which are free of disadvantages and complications associated with prior art processes.

It is an aspect of the invention to provide for an improved process for the manufacture of hindered aryl phosphites by mixing a substantially stoichiometric amount of 2,4-dialkyl phenol with a phosphorous trihalide in methylene chloride with a relatively large amount of pyridine. Reaction is carried out in at 0–5° C. which takes 1 h for the completion and one hour for isolation in isopropanol.

It is well recognized to the persons skilled in the art that the amount of Lewis base used in synthesis of sterically hindered triaryl phosphites have traditionally been only several mole percent, or a fraction of a mole percent, compared to aryl reagents. However, according to the present invention, the use of a relatively large amount of Lewis base results in the ability of the reaction to go to its completion at a faster rate, and at a lower temperatures. This unexpected result has a technological and economic advantage over the prior art. Large amount of Lewis base means 10 mole percent or more of the Lewis base compared to the substituted phenol, preferably over 20 mol %, more preferably over 50 mol %, and most preferably the amount of the Lewis base is about stoichiometrically equivalent to the substituted phenol.

In yet another aspect a process for producing triaryl phosphite of (Structure 2) has been provided wherein $R_a$ is tertiary alkyl, $R_b$ is lower alkyl or tertiary alkyl, the process comprises reacting $PCl_3$ with 2,4-dialkyl phenol of formula ROH where $R=C_6H_3R_aR_b$ ($R_a$ is tertiary alkyl, $R_b$ is lower alkyl or tertiary alkyl) (Structure 1) wherein the reaction is carried out by adding $PCl_3$ to a solution of 2,4-dialkyl phenol in methylene chloride and pyridine at 0–5° C. under nitrogen atmosphere over a period of one hour. After methylene chloride has been distilled out and isopropanol has been added to precipitate white crystalline solid, which is filtered out and is washed with cold methanol.

In still another aspect, the invention provides for a process of reacting 2,4-ditertiary butyl phenol with PCl₃ to produce tris-(2,4-ditertiaryl butyl phenyl) phosphite as illustrated in Structure 3.

In yet another aspect, the invention provides for a process of reacting 2,4-di tertiary amyl phenol with PCl₃ to produce tris(2,4-ditertiaryl amyl phenyl)phosphite as illustrated in Structure 4.

In still another aspect, the invention provides for a process of reacting 2-tertiary butyl-4-methyl phenol with PCl₃ to produce tris (2-tert butyl-4-methyl phenyl) phosphite as illustrated in Structure 5.

DETAILED DESCRIPTION OF THE INVENTION

The present invention relates a novel process for the production of tris (2,4-ditertiary butyl phenyl) phosphite, tris (2,4-ditertiary amyl phenyl) phosphite and 2-tertiary butyl-4-methyl phenyl phosphite especially in large scale manufacturing. Large scale manufacturing requires the production of title compound in a cost efficient manner. This led to the enquiry into producing the title compound with lesser impurity and with a better yield. Also one of the concerns was to achieve the desired lower temperature so as to have high yield with shortened reaction time.

The hydrogen chloride formed in the reaction PCl₃ with the phenol is removed by one of the following methods:
 by removing HCl time to time by applying vacuum,
 by passing CO₂ gas,
 by refluxing at high temperatures,
 by using a Lewis base.

All the above methods are laborious and time consuming. Therefore they are not suitable for commercial production of the title compound. The method employing the use of a Lewis base is more suitable in this case. The bases that can be conveniently used are triethylamine, trimethylamine and pyridine. Results were found to be good in the case of pyridine as base compared with the other two.

A process for producing triaryl phosphite has been provided. The process involves making triaryl phosphite of formula (Structure 2) comprising of reacting PCl₃ with 2,4-dialkyl phenol of formula (Structure 1). Aforesaid reaction is being carried out by adding PCl₃ to a solution of 2,4-dialkyl phenol in methylene chloride and pyridine at 0–5° C. under nitrogen atmosphere over a period of one hour. After distilling out methylene dichloride and addition of isopropanol the resultant white crystalline precipitate was filtered out. Washing of this precipitate with cold methanol gives the product.

In the given formulae, $R_a$ and $R_b$ may be various organic substituents. They may be alkyl, aryl, alkene, alkanyl, cycloalkyl, cycloalkene, and a combination thereof. Furthermore, such organic substituents may have any number of non-carbon groups on them, as long their presence does not interfere with the reaction to obtain triaryl phosphite. The preferred organic substituents are saturated alkyl substituents, more preferably branched chains, most preferably containing one to six carbons.

Although PCl₃ was used within our experiments, other phosphorus trihalides may be used. Examples of other halogens that may be used include fluorine, bromine, and iodine, thus it is possible that under appropriate method modifications, in place of PCl₃ one may use PF₃, PBr₃, PI₃. It is also recognized that a mixture of halides substituents on the phosphorus center may be used, exemplified by PCl₂Br, PClBr₂, PCl₂I, POlI₂, PBr₂I, and PBrI₂. Furthermore, a mixture of various phosphorus trihalide compounds may be used to obtain the desired triaryl phosphite; instead of essentially pure PCl₃, one may use a mixture PCl₃ and PBr₃, a mixture of PCl₃ and PI₃, a mixture of PCl₃, PCl₂Br, PClBr₂, PBr₃, and other similar trihalide mixtures.

Structure 1

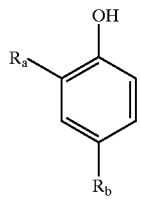

Structure 2

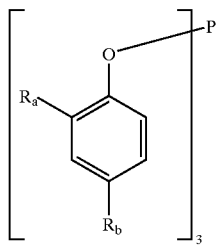

$R_a$ = tert alkyl
$R_b$ = tert alkyl or lower alkyl

In another embodiment, in the process as described above, 2,4-ditertiary butyl phenol is reacted with PCl₃ to produce tris-(2,4-di-tert-butyl phenyl) phosphite (Structure 3).

Structure 3

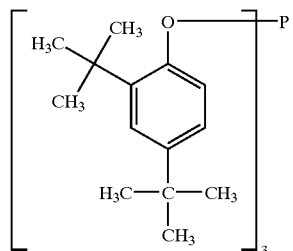

In another embodiment, 2,4-di tertiary amyl phenol is reacted with PCl₃ to produce tris(2,4-ditertamyl phenyl) phosphite (Structure 4) in the process as illustrated in Structure 1 and Structure 2 above.

Structure 4

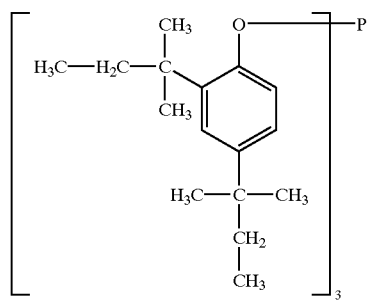

In yet another embodiment, the invention is addressed at reacting 2-tertiary butyl-4-methyl phenol with PCl₃ to produce tris (2-tert butyl-4-methyl phenyl) phosphite as illustrated in Structure 5.

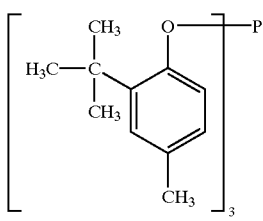

Structure 5

Preferred embodiments are further illustrated in the following examples:

EXAMPLE 1

Preparation of tris (2,4-di tertiary butyl phenyl) phosphite

A 500 mL 3-necked flask equipped with a thermometer, an addition funnel, and a nitrogen/vacuum inlet attached to a Schlenk line manifold, was charged with 61.9 g (0.3 mole) of 2,4-ditertiary butyl phenol (Ciba Specialty Chemicals), 23.7 g (0.3 mole) of pyridine in 200 ml methylene dichloride. 13.75 g (0.1 mole) of $PCl_3$ (Ciba Specialty Chemicals) was then added dropwise at a temperature of 0 to 5° C. under nitrogen atmosphere a period of 30 to 40 minutes. After the addition, the addition funnel was replaced with a distillation apparatus, and methylene chloride was distilled out at 40° C. After addition of 100 ml isopropanol to the residue, the resultant white crystalline precipitate was then filtered and washed with cold methanol several times. The product weighed 60.72 g (94% of the theoretical yield). Material showed HPLC purity of 99.99% and melted at 181–182° C. (lit value: 182° C.).

EXAMPLE 2

Preparation of tris (2,4-di tertiary amyl phenyl) phosphite

A 500 mL 3-necked flask equipped with a thermometer, an addition funnel, and a nitrogen/vacuum inlet attached to a Schlenk line manifold, was charged with 70.2 g (0.3 mole) of 2,4-ditertiary amyl phenol (Chemicals Unlimited, Mumbai, India), 23.7 g (0.3 mole) of pyridine in 200 ml methylene dichloride. 13.75 g (0.1 mole) of $PCl_3$ was then added drop-wise at a temperature of 0 to 5° C. under nitrogen atmosphere a period of 30–40 minutes. After the addition, the addition funnel was replaced with a distillation apparatus, and methylene chloride was distilled out at 40° C. After addition of 100 ml isopropanol to the residue, the resultant white crystalline precipitate was then filtered and washed with cold methanol several times. The product weighed 68.6 g (94% of the theoretical yield). Material showed HPLC purity of 99.99% and melted at 106–108° C. (lit value: 108° C.).

EXAMPLE 3

Preparation of tris (2-tertiary butyl-4-methyl phenyl) phosphite

A 500 mL 3-necked flask equipped with a thermometer, an addition funnel, and a nitrogen/vacuum inlet attached to a Schlenk line manifold, was charged with 49.2 g (0.3 mole) of 2-tertiary butyl-4-methyl phenol, 23.7 g (0.3 mole) of pyridine in 200 ml methylene dichloride. 13.75 g (0.1 mole) of $PCl_3$ was then added drop-wise at a temperature of 0 to 5° C. under nitrogen atmosphere over a period of 30 to 40 minutes. After the addition, the addition funnel was replaced with a distillation apparatus, and methylene chloride was distilled out at 40° C. After addition of 100 ml isopropanol to the residue, the resultant white crystalline precipitate was then filtered and washed with cold methanol several times. The product weighed 48.8 g (94% of the theoretical yield). Material showed HPLC purity of 99.99% and melted at 114–115° C.(lit value: 115° C.).

EXAMPLE 4

Recycling of Solvents and Lewis Base

Several series of experiments are carried out to illustrate the excellent results observed when the solvent filtrate was subjected to recovery of pyridine and isopropanol.

The filtrate containing IPA and pyridine hydrochloride was subjected for distillation at 50° C. under reduced pressure to recover 95% isopropanol. The residue obtained was stirred with sodium hydroxide flakes and then subjected to distillation to recover 95% of pyridine. Purity of the solvent and base was >99% by GC and excellent results were obtained after reuse.

What is claimed is:

1. A method of producing triaryl phosphites of the formula $P(OR)_3$, by reacting a di alkyl substituted phenol of formula ROH with phosphorus trihalide at a temperature of 0–5° C. under a nitrogen atmosphere in a presence of a Lewis base, wherein R represents an aryl compound of a formula $C_6H_3R_aR_b$, wherein $R_a$ is tertiary alkyl substituent, $R_b$ is lower alkyl or tertiary alkyl substituent.

2. A method according to claim 1, wherein said Lewis base is a heterocyclic amine compound.

3. A method according to claim 2, wherein the relative amount of said heterocyclic amine compound is more than 10 mol % of the amount of said aryl compound of a formula $C_6H_3R_aR_b$.

4. A method according to claim 2, wherein the relative amount of said heterocyclic amine compound is more than 20 mol % of the amount of said aryl compound of a formula $C_6H_3R_aR_b$.

5. A method according to claim 2, wherein the relative amount of said heterocyclic amine compound is more than 50 mol % of the amount of said aryl compound of a formula $C_6H_3R_aR_b$.

6. A method according to claim 2, wherein the relative amount of said heterocyclic amine compound is about equal to the amount of said aryl compound of a formula $C_6H_3R_aR_b$.

7. A method according to claim 5, wherein $R_a$ and $R_b$ of said aryl compound of a formula $C_6H_3R_aR_b$ is substituted in the 2,4-position.

8. A method according to claim 7, wherein said $R_a$ or $R_b$ is an alkyl substituent.

9. A method according to claim 8, wherein said alkyl substituent is branched or straight chain with one to six carbons.

10. A method according to claim 8, wherein said alkyl substituent is selected from a group consisting of methyl, tertiary butyl, and tertiary amyl substituents.

11. A method according to claim 8, wherein $R_a$ is a tertiary butyl substituent.

12. A method according to claim 11, wherein $R_a$ is in the 2-position on the aryl compound.

13. A method according to claim 12, wherein $R_b$ is a tertiary butyl substituent.

14. A method according to claim 12, wherein $R_b$ is a methyl substituent.

15. A method according to claim 8, wherein $R_a$ is a tertiary amyl substituent.

16. A method according to claim 9, wherein $R_b$ is a tertiary amyl substituent.

17. A method according to claim 4, wherein $R_a$ and $R_b$ of said aryl compound of a formula $C_6H_3R_aR_b$ is substituted in the 2,4-position.

18. A method according to claim 17, wherein said $R_a$ or $R_b$ is an alkyl substituent.

19. A method according to claim 18, wherein said alkyl substituent is branched or straight chain with one to six carbons.

20. A method according to claim 18, wherein said alkyl substituent is selected from a group consisting of methyl, tertiary butyl, and tertiary amyl substituents.

21. A method according to claim 8, wherein $R_a$ is a tertiary butyl substituent.

22. A method according to claim 21, wherein $R_a$ is in the 2 position on the aryl compound of a formula $C_6H_3R_aR_b$.

23. A method according to claim 22, wherein $R_b$ is a tertiary butyl substituent.

24. A method according to claim 23, wherein $R_b$ is a methyl substituent.

25. A method according to claim 18, wherein $R_a$ is a tertiary amyl substituent.

26. A method according to claim 20, wherein $R_b$ is a tertiary amyl substituent.

27. A method according to claim 1, wherein reaction completion time is one hour.

28. A method according to claim 1, wherein the reaction is a one pot synthesis suitable for economically viable commercial production.

* * * * *